United States Patent [19]

Shinitzky et al.

[11] Patent Number: 4,474,773
[45] Date of Patent: Oct. 2, 1984

[54] LIPID FRACTION FOR TREATING DISEASE

[75] Inventors: Meir Shinitzky, Rehovot; David Heron, Tel Aviv; David Samuel, Rehovot, all of Israel

[73] Assignee: Yeda Research and Development Co., Ltd., Israel

[21] Appl. No.: 377,959

[22] Filed: May 13, 1982

[30] Foreign Application Priority Data

Sep. 4, 1981 [IL] Israel ........................................ 63734

[51] Int. Cl.$^3$ ............................................ A61K 31/685
[52] U.S. Cl. ..................................... 424/199; 424/365
[58] Field of Search ................................ 424/199, 365

[56] References Cited

U.S. PATENT DOCUMENTS

| | | | |
|---|---|---|---|
| 3,752,832 | 8/1973 | Maruyama et al. | 260/398.5 |
| 4,157,404 | 6/1979 | Yano et al. | |
| 4,221,784 | 9/1980 | Growdon et al. | 424/199 |
| 4,254,115 | 3/1981 | Dawidson et al. | 424/211 |
| 4,263,286 | 4/1981 | Nakajima et al. | 424/199 |
| 4,372,949 | 2/1983 | Kodama et al. | 424/199 |

OTHER PUBLICATIONS

Murata et al., J. Nutrition, vol. 112, (1982), pp. 1805–1808.

*Primary Examiner*—Sam Rosen
*Attorney, Agent, or Firm*—Bernard, Rothwell & Brown

[57] ABSTRACT

The invention concerns novel lipid extracts obtainable from natural sources such as egg, yolk or soyabean; and useful for treating various diseases and physiologic conditions.

29 Claims, No Drawings

LIPID FRACTION FOR TREATING DISEASE

FIELD OF THE INVENTION

The present invention relates to a process for the fractionation of lipids from natural sources into various fractions, the fraction of choice being one with a substantially increased potential for fluidization as well as for the restoration of impaired functions of biological membranes, when compared with other lipid preparations. The invention further relates to the fractions thus separated, and to pharmaceutical compositions comprising such fractions. The invention further relates to the treatment of various disorders connected with abnormalities in the structure and dynamics of membranes such as dysfunction of the immune system, drug addiction and alcoholism, hypertension, and hyperlipidemic disorders such as gallstones; and atherosclerosis. The in vivo treatment comprises administering an effective quantity of such fractionated lipids. Treatment of other dysfunctions, such as sperm infertility, can also be carried out in vitro.

Other and further objects of the invention will become apparent hereinafter.

BACKGROUND OF THE INVENTION

The lipid fluidity (reciprocal of misroviscosity-$\bar{\eta}$) of biological membranes is determined by their structure and chemical composition and, in particular, the mole ratio of cholesterol to phospholipids (C/PL), the mole ratio of sphingomyelin to lecithin (S/L) and the degree of unsaturation of the phospholipid acyl chains (Shinitzky and Henkart, Int.Rev.Cytol. 60, 121 (1979); Cooper, J., Supramol.Struct. 8, 413 (1978)).

The membrane lipid fluidity, in turn determines many of the physiological properties of receptors (Muller and Shinitzky, Brit.J.Haematol. 42, 355 (1979); Heron, et al., Proc.Natl.Acad.Sci. USA, 77, 7463 (1980); Heron et al., in "Receptors and their Neurotransmitters", eds. Littauer et al., John Wiley, London (1980); Heron et al., Eur.J.Pharmacol. 72, 361 (1981), antigens (Shinitzky and Souroujon, Proc.Natl.Acad.Sci. USA 76, 4438 (1979) enzymes (Sandermann, Biochim.Biophys.Acta, 515, 209 (1978); Rimon et al., Nature, 270, 267 (1977), transport carriers (Kimelberg, Biochim.Biophys.Acta, 413, (1975), ion channels (Stephens and Shinitzky, Nature, 270, 267 (1977), and ribosomes (Towers et al., Biochim.Biophys.Acta, 287, 301 (1972) which are bound to these membranes in the brain and other organs. This subject was recently extensively reviewed (Shinitzky, Physiol. Rev. in press).

The final response of target cells depends, therefore, on the structural and dynamic properties of their membranes, which are determined by their lipid composition. One may, therefore, expect an optimal lipid fluidity for the maximal response of each target cell (Heron et al., Proc.Natl.Acad.Sci. USA, 77, 7463 (1980); Heron et al., in "Receptors and their Neurotransmitters", eds. Littauer et al., John Wiley, London (1980); Yuli et al., Biochemistry, 20, 4250, (1980); Shinitzky, Physiol. Rev., in press).

In many disorders, the pathogenesis involves changes in membrane lipid composition or lipid metabolism (Cooper, N.Engl.J.Med., 297, 371 (1977)). These changes have been correlated in many cases to an increase in membrane lipid miscroviscosity of various tissues due to an increase in C/PL or S/L or a decrease in the degree of unsaturation of the phospholipid acyl chains or any combination of the three. Lipid peroxidation can also affect the dynamics of cell membrane proteins and consequently the overt physiological functions (Sagai and Ichinose, Life Sci., 27, 731 (1980)). The following is a list of such disorders mediated by lipid imbalances, all of which are amenable to lipid manipulations:

(1) Aging and senescence (Yamamoto, Lipids, 3, 284 (1968); Rivnay et al., Mech. Age. Dev. 10, 71 (1979); Heron et al., to be published; see also Table 4 in this specification; Araki and Rifkind, Life Sci. 26, 2223 (1980); Hershkowitz et al., Progress in Brain Research, Elsevier-North Holland, in press); Rouser et al., Avd. Lipid Res. 10, 262 (1972).

(2) Withdrawal symptoms of drug and alcohol addiction (Johnson et al., Mol.Pharmacol., 15, 739 (1979); Chin and Goldstein, Science, 196, 684 (1979); Littleton and John, J.Pharm.Pharmac., 29, 579 (1977); Heron et al., Biochem,Pharmacol. in press (1982); see also Table 3 in this specification).

(3) Hyperlipidemic disorders such as hypertension, atherosclerosis, gallstones, cirrhosis, and obesity (Montenay et al., Biochem.Biophy.Res.Comm. 100, 660 (1981); Cooper, N., Engl.J.Med., 297, 371 (1977); Miettinen et al., Lancet 2, 835 (1972).

(4) Sperm infertility (Davis et al., Biochim.Biophys. Acta, 558, 257 (1979); Davis, Proc.Soc.Exp.Biol.Med., 152, 257 (1976)).

(5) Impaired immune function such as in aging, obesity and certain cases of allergies (Rivnay et al., Mech.Age.Dev., 12, 119 (1980); Rivnay et al., Mech.Age.-Dev. 10, 71 (1979).

We have also shown that synaptic membrane microviscosity increases as a result of surgical or chemical lesions of specific pathways in the brain (Heron et al., Biochem.Pharmacol., in press (1982). These findings may apply to other degenerative or organic damages such as Alzheimer's disease, Parkinsonism, Tardive dyskinesia, Huntington's chorea, tremor, ataxia, and epilepsy and certain cases of mental retardation, all of which could in principle be treated by lipid manipulation.

It is also generally accepted that certain mental disorders such as mania, depression and schizophrenia are related to a chemical imbalance in the turnover rate of neutrotransmitters in the brain. There is evidence to suggest that the biogenic amines (dopamine, norephinephrine and serotonin) are primarily involved. The receptors and membranes bound enzymes concerned with turnover of these transmitters can be altered by changes in membrane fluidity (Hershkowitz et al., Progress in Brain Research, Elsevier-North Holland, in press; Heron et al., Proc.Natl.Acad.Sci. USA 77, 7463 (1980); Heron et al., in "Receptors and Their Neurotransmitters", eds. Littauer et al., John Wiley, London (1980); Heron et al., Eur. J.Pharmacol., 72, 361 (1981), and therefore also falls into the category of disorders amenable to lipid manipulations.

Modulation of function by lipid manipulations can also be carried out in vitro. This could be applicable to modulation of viral infectivity for use in vaccinations (Pal et al., Biochemistry 20, 530 (1981), and antigenicity (Shinitzky and Souroujon, Proc. Natl.Acad.Sci., USA 76, 4438 (1979)), which could reduce tissue rejection and facilitate transplatations.

We have found that some of the adverse effects mediated by lipid imbalances could be rectified by a form of "membrane engineering", through the use of an active fraction of lipids from natural sources. This fraction (which contains a substantial portion of lecithin) can operate via several possible mechanisms:

(1) Extraction of excess cholesterol by passive translocation (Cooper, J.Supramol.Struct., 8, 413 (1978); Miettinin et al., Lancet, 2, 835 (1972); Morison, Geriatrics 13, 12 (1958); Cooper et al., J.Clin.Invest. 55, 115 (1975)).

(2) Exchange with membrane lipids of higher microviscosity (Wirtz and Zilversmit, Biochim.Biophys. Acta 193, 105 (1969).

(3) Net incorporation into or replacement of damaged lipids (e.g. peroxidized) (Bakardjieva et al., Biochemistry 18, 3016 (1979)). This could restore the structure and function of degenerate membranes.

(4) Precursors in various metabolic pathways (e.g. prostaglandins, vitamin D and acetylcholine).

However, diets having a high content of lecithin, which are frequently recommended for a variety of disorders (Cobb et al., Nutr.Metab., 24, 288 (1980); Blass (Cornall-Burke Rehabilitation Center); Gershon (Lafayette Clinic, Detroit); Heyman (Duke University Med. Center); Sullivan et al., (M.I.T. and Tufts Univ.), in "Proceedings of the International Study Group on the Pharmacology of Memory Disorders Associated with Aging", Zurich (1981)), are not very effective in alleviating symptoms associated with lipid imbalances and in restoring membrane lipid fluidity to normal. The reasons for this are not yet clear. It seems that the previously proposed rationale for these lecithin treatements, which are based either on its acetycholine precursor role or on the high degree of unsaturation covers only a minor aspect of this approach (Herring et al., Biochim.-Biophys.Acta 602, 1 (1980); Shinitzky and Henkart, Int. Rev. Cytol. 60, 121 (1979)).

It is plausible that the process of lipid manipulation combines several prerequisites such as the following:

(1) Fluidization is effected by a well defined portion of the lipids, while the rest serve as essential carriers which facilitate transport and absorption into the membranes.

(2) The assembly of the active and the carrier components is of defined physico-chemical characteristics, such as the surface density and charge distribution.

(3) These characteristics could be optimal for proper transportation, associated with cell surfaces, disintegration, unloading or exchange, as dictated by the site of interaction.

(4) The various lipid components could act synergistically to effect the activities described above.

(5) The degree of unsaturation is optimal, i.e. it has the necessary fluidity characteristics (the transition from fully saturated to mono-unsaturated is the most critical to fluidizing ability, while the transition from mono to poly-unsaturated does not significantly change the fluidizing ability (Hubbel and McConnell, J.Am.Chem.Soc. 93, 314 (1971); Stubbs et al., Biochemistry 20, 4257 (1981)), and yet not too unsaturated, thus less vulnerable to oxidation.

SUMMARY OF THE INVENTION

According to the present invention there is provided a novel process for the fractionation of lipids and preferably of lipid extract, from natural sources, into at least two fractions, one of these, the one to be used for purposes of the present invention, having a substantially higher potential for membrane fluidization than other preparations. This fraction is hereafter referred to as "active lipid", (AL), and is a novel composition of matter, which is characterized by a high potency of membrane fluidization.

The invention further relates to the use of AL in the treatment of various diseases and anomalous states in mammals and also in humans and to pharmaceutical compositions for such treatments. Amongst conditions amenable to treatment by means of the compositions according to the invention are the following:

1. Increased vulnerability to bacterial contaminations;
2. Dysfunctions of the immune system;
3. Allergies;
4. Hypertension;
5. Hyperlipidemic states such as atherosclerosis, gallstones, cirrhosis and obesity, and the like;
6. Symptoms of withdrawal from alcohol and other drugs;
7. Prevention of tolerance to drugs.

The invention further relates to the use of AL (in vitro or in vivo) in the treatment of infertility, viral and microbial contaminations, and reduction of tissue antigenicity which could reduce tissue rejection and facilitate transplantations etc.

The invention further relates to the treatment of the above mentioned disorders, by administering (either in vivo or in vitro) effective quantities of AL having a substantially increased capacity for membrane fluidization compared with other lipid preparations.

The fractionation is effected by dissolving a lipid extract from a biological source (e.g. egg yolk, soybean) in a suitable solvent, evaporating the solvent to almost complete dryness and precipitating a fraction of the dissolved lipids by addition of an organic solvent, and recovering the desired fraction from the supernatant by evaporation of the solvent. This fraction is supplemented with a 0.5% (w/w) tocopherol or any other suitable antioxidant. Alternatively, the fractionation is effected by treating the lipid source (e.g. egg yolk, soybean) with a suitable solvent, removing the precipitate and then dissolving it again in a suitable solvent and recovering the supernatant. The desired fraction is then recovered from the supernatant either by evaporation of the solvent or by precipitation in the cold and then evaporation of the traces of the solvent. This fraction is also supplemented with 0.5% (w/w) tocopherol or any other suitable antioxidant.

The three preferred embodiments of the invention are the following:

(1) The lipid extract from egg yolk (e.g. crude lecithin) is dissolved in chloroform, evaporated to almost dryness, acetone is added to effect a precipitation of a certain part of the lipid, and the supernatant is removed, evaporated and the solvent is removed to complete dryness, leaving a fraction of about 5 weight percent of the initial quantity of the untreated egg-yolk, which is the desired fraction AL. An antioxidant such as tocopherol is added to a final concentration of about 0.5% (w/w). Analysis of the lipid composition of this fraction (Preparation 1) is given in Table 1.

(2) A natural lipid source (e.g. egg yolk, soybean) is first mixed with acetone to remove excess undesired lipids. The precipitate is then treated again with acetone, and the supernatant is collected, evaporated to complete dryness, leaving a fraction of about 10-15 weight percent of the initial quantity of the untreated egg-yolk, which is the desired fraction AL. An antioxidant such as tocopherol is added to a final concentration of about 0.5% (w/w). Analysis of the lipid composition of this fraction (Preparation 2) is also given in Table 1. Amongst other solvents which can be used there may be mentioned: chloroform-methanol 1:1 v/v, hexane, tetrahydrofuran, acetonitrile, ethanol, methanol, diethyl ether and diethyl ketone.

(3) A natural lipid source (e.g. egg-yolk, soybean) is first mixed with acetone to remove excess undesired lipids. The precipitate is then treated again with acetone, and the supernatant is collected and cooled below 0° C., upon which the desired fraction (AL) amounting to about 10-15 weight percent of the initial quantity of the untreated egg-yolk, is precipitated and collected. An antioxidant such as tocopherol is added to a final concentration of about 0.5% (w/w). Analysis of the lipid composition of this fraction (preparation 3) is given in Table 1 and 2. Amongst other solvents which can be used there may be mentioned: chloroform-methanol 1:1 v/v, hexane, tetrahydrofuran, acetonitrile, ethanol, methanol, diethyl ether and diethyl ketone.

DESCRIPTION OF THE PREFERRED EMBODIMENT

The lipids are extracted from a quantity of 10 g dried egg yolk by first mixing with 50 ml of acetone. The precipitate is removed and then treated with 50 ml chloroform and the solution, which contains the lipid extract, is collected. The chloroform is then removed under reduced pressure to almost dryness. A quantity of 50 ml of cold (5°-10° C.) acetone is added, and this results in a precipitation of the majority of the lipids within 1-3 hours. This precipitate is discarded, the supernatant is collected and the acetone is completely evaporated. There remains the desired fraction of active lipids (AL) weighing 0.8-1.2 grams. This fraction is supplemented with 0.5% (w/w) tocopherol. The composition of this preparation (#1) is given in Table 1.

A modified procedure (#2) which yields similar results is described in the following: 10 ml of fresh egg yolk is mixed with 30-40 ml acetone and stirred for 5 minutes at room temperature. The precipitate is collected and extracted with 30-40 ml of fresh acetone at 40°-45° C. for 30-60 minutes. The supernatant is collected and evaporated to complete dryness. There remains the desired fraction of 1.0-1.5 gram active lipids (AL). This fraction is supplemented with 0.5% tocopherol. The composition of this preparation (#2) is also given in Table 1.

Preparation #3 is prepared as follows: One volume of fresh egg-yolks is mixed with 2-3 volumes of acetone containing 1 mg/ml vitamin E (α-tocopherol acetate) at room temperature for 5 minutes. The solid material is separated and treated with 2 volumes of fresh acetone at 40°-45° C. for 1 hour. The acetone extract is separated from the solid residue by fast filtration and is cooled to −20° C. for 16 hours, upon which the Active Lipid (AL) precipitates out. AL is separated by fast filtration, washed with ethanol and exhaustively dried (under vacuum). The product is supplemented with 0.5% vitamin E. The yield is 10-15 gr out of 100 gr wet egg yolks.

TABLE 1

| Composition of AL | | | |
|---|---|---|---|
| | Preparation #1 weight % | Preparation #2 weight % | Preparation #3 weight % |
| Neutral lipids (total) | 50-70 | 70-80 | 65-75 |
| (a) glycerides | 40-60 | 60-70 | 60-70 |
| (b) cholesterol | 3-5 | 3-5 | 3-5 |
| (c) others | less than 5 | less than 5 | less than 5 |
| Lecithin (phosphatidyl choline) | 20-50 | 10-20 | 15-25 |
| Phosphatidyl ethanolamine | 10-15 | 5-10 | 5-10 |
| Negatively charged Phospholipids | 2-5 | 2-5 | 2-3 |
| Unsaturated/saturated fatty acids | above 2 | above 2 | above 1 |

TABLE 2

| Fatty Acid Composition of Preparation #3 (A Typical Example) | | | | | |
|---|---|---|---|---|---|
| Fatty acid | AL | diglycerides | NL triglycerides | PC | PE |
| 16:0 | 39.8 | 42.5 | 27.6 | 42.8 | 33.3 |
| 16:1 | 2.5 | 5.0 | 14.5 | — | — |
| 18:0 | 6.6 | 5.8 | 12.3 | 13.5 | 15.1 |
| 18:1 | 42.5 | 40.0 | 26.3 | 34.8 | 42.7 |
| 18:2 | 8.2 | 6.6 | 19.3 | 8.9 | 8.9 |
| 20:4 | 0.4 | — | — | — | — |

The activity of AL as a lipid fluidizer, is demonstrated in the following experiments. Mouse brain membranes (Crude mitochondrial fraction—$P_2m$, prepared from the mouse forebrain) was incubated with lipid dispersion in 50 mM Tris-HCl buffer pH 7.4 containing 3.5% polyvinyl pyrrolidone (PVP) (0.2 mg/ml) for 30 minutes at room temperature, with constant shaking (Heron, et al., Proc. Natl. Acad. Sci. USA 77, 7463 (1980). The final concentration of lipids was 0.04 mg lipids per 1 mg $P_2m$ membranes. The membranes were then extensively washed and the lipid microviscosity ($\bar{\eta}$) was determined according to Shinitzky and Barenholz, Biochim. Biophys. Acta 515, 367 (1978). The cholesterol and phospholipid content were determined according to Bartlett, J. Biol. Chem. 234, 466 (1959), and Brown et al., Anal. Chem. 26, 367 (1954), respectively. It can be clearly seen in Table 3 that AL is superior to all other lipids tested in its fluidizing potency. It can be also seen in Table 3 that the fluidization is effected both by cholesterol extraction and by net incorporation of the phospholipids. Similar experiments with mouse spleen cells were carried out. The cells ($10^6$/ml) were incubated with lipid dispersion (0.3 mg/ml) in phosphate-buffered saline (PBS) containing 3.5% PVP for 2 hours at 37° C., and then washed extensively (Shinitzky et al. Proc. Natl. Acad. Sci. USA 76, 5313 (1979). The results are summarized in Table 4. Again, it can be clearly seen that AL is much more potent than PC in its fluidizing capacity.

TABLE 3

| The effects of various lipids on the microviscosity ($\bar{\eta}$) of mouse membranes($P_2m$) and their cholesterol (C) and phospholipid (PL) content | | | | |
|---|---|---|---|---|
| Treatment | $\bar{\eta}$ (25° C., poise) | C/protein (w/w) | PL/protein (w/w) | C/PL (M/M) |
| Control | 4.7 ± 0.2 | 4.1 ± 0.3 | 1.0 ± 0.2 | 0.33 ± 0.4 |

TABLE 3-continued

The effects of various lipids on the microviscosity ($\bar{\eta}$) of mouse membranes($P_2m$) and their cholesterol (C) and phospholipid (PL) content

| Treatment | $\bar{\eta}$ (25° C., poise) | C/protein (w/w) | PL/protein (w/w) | C/PL (M/M) |
|---|---|---|---|---|
| (Vehicle treated) AL (Preparation #3) | 2.8 ± 0.3 | 2.3 ± 0.3 | 1.8 ± 0.3 | 0.11 ± 0.2 |
| Crude egg-lecithin "Sigma", Grade II) | 4.0 ± 0.1 | 3.6 ± 0.2 | 1.1 ± 0.2 | 0.27 ± 0.4 |
| Pure egg-lecithin (PC) ("Lipid-Products", Nutfield, England) | 4.1 ± 0.2 | 3.3 ± 0.4 | 1.5 ± 0.3 | 0.18 ± 0.3 |
| Dipalmitoyl-lecithin (DPL) (Koch-Light Labs, Colnbrook, England | 6.4 ± 0.2 | — | — | — |

The results represent the mean ± S.D of at least 10 experiments, each with a different batch of AL.

TABLE 4

The effect of various lipids on the microviscosity ($\bar{\eta}$) of mouse spleen cells.

| Treatment | $\bar{\eta}$ (25° C., poise) |
|---|---|
| Control | 3.5 ± 0.2 |
| Vehicle treated AL (Preparation #3) | 2.3 ± 0.3 |
| PC ("Lipid products" Nutfield, England) | 3.3 ± 0.2 |

The results represent the mean ± S.D. of at least 5 experiments, each with a different batch of AL.

In addition to being useful for in vitro manipulations, as described above, the above AL fractions can be used as an active ingredient in drugs administered to warm blooded mammals for the treatment of conditions where the structure and dynamics of the membrane lipids is impaired.

The effective quantities of the fraction vary with the condition treated and the needs of the patient, but the effective quantities for warm blooded mammals are in the order of from 1 g to 20 g per patient per day. The novel fraction is advantageously administered intraveneously in the form of lipid suspension in saline (10–100 mg/ml).

For the in vitro manipulations the effective quantities are in the order of 50–200 mg/$10^6$ cells in 1 ml medium. Such in vitro manipulations may be used to treat sperm infertility, facilitate tissue transplantations or to modulate viral infectivity for use in vaccinations.

SUPPORTIVE RESULTS (1) Reduction of the Withdrawal Symptoms in Morphine Addicted Mice Four groups of male Balb/C mice were injected subcutaneously with morphine (between 40 and 200 mg/kg twice daily for eight days). On the 9th day each group was injected intraperitoneally with (a) saline (0.3 ml), (b) dipalmitoyl lecithin (a synthetic fully saturated membrane rigidifying agent), (c) AL by i.p. injection, or (d) AL given in the diet. All four groups were then injected with 2.5 mg/kg naloxone, a morphine antagonist known to precipitate withdrawal symptoms. These symptoms were then scored in an observation chamber and the results are shown in Table 5.

The microviscosity of the synaptic membranes from the different regions of the brain, was measured by fluorescence polarization using diphenylhexatriene (DPH) as a probe, by the method of Shinitzky and Barenholz, Biochim. Biophs.Acta 515, 367 (1978). The results are also given in Table 5, and are compatible with the suggestion that membrane microviscosity ( ) is increased during chronic morphine intake. This is probably due to an increase in C/PL so as to compensate for the fluidizing effects of the drug. Similar results have been reported by others (Johnson et al., Mol.Pharmacol. 15, 739 (1979); Chin and Goldstein, Science 196, 684 (1977) for alcohol addiction.

It can be seen in Table 5 that the withdrawal symptoms were aggravated by dipalmitoyl lecithin (which induces an increase in membrane microviscosity), and reduced, or almost entirely eliminated, by AL—both when injected or given in the diet, with concomitant decreases in membrane microviscosity.

As was mentioned above, chronic alcoholism also involves increased cholesterol in synaptic membranes, in order to compensate for the fluidizing effects of alcohol, and therefore alcohol withdrawal is also amenable to treatment by AL.

Finally, since the process of adaptation (i.e. tolerance) to morphine and other drugs involves increase in C/PL mole ratio in the membranes, AL given in conjunction with drugs such as morphine etc. could prevent the development of tolerance and therefore the decreased potency of such drugs. This approach could be of paramount importance, for example in cases of terminal cancers receiving morphine to ease the pain.

TABLE 5

The effect of lipids on naloxone-precipitated withdrawal symptoms and on brain membrane lipid fluidity in morphine dependent mice.

| | AL n = 32 | Saline (Control) n = 28 | Dipalmitoy Lecithin n = 16 | Al Diet n = 10 |
|---|---|---|---|---|
| Jumps | 3 ± .07(*) | 21 ± 4 | 35 ± 8(+) | 11 ± 4.4(#) |
| Body shakes | 4 ± .9(*) | 17 ± 2.5 | 19 ± 2.3(n.s) | 4 ± 1.6(*) |
| Forelimb tremor[1] | <40% | >80% | >90% | <60% |

TABLE 5-continued

The effect of lipids on naloxone-precipitated withdrawal symptoms and on brain membrane lipid fluidity in morphine dependent mice.

|  | AL<br>n = 32 | Saline<br>(Control)<br>n = 28 | Dipalmitoy<br>Lecithin<br>n = 16 | Al Diet<br>n = 10 |
|---|---|---|---|---|
| Diarrhea[2] | <50% | >90% | >90% | <75% |
| Writhing[3] | <50% | >75% | >90% | <50% |
| Penile ejaculation[4] | >75% | >50% | >50% | >75% |
| $\bar{\eta}$, 25° C. (poise) | | | | |
| Hippocampus | 5.95 ± 0.03(*) | 6.41 ± 0.04 | 6.58 ± 0.07(∇) | 6.10 ± 0.7(*) |
| Caudate | 6.41 ± 0.06(*) | 6.75 ± 0.05 | 6.75 ± 0.08(n.s.) | 6.58 ± 0.09(+) |

(*) - p <0.001,
(∇) - p <0.025,
(+) - p <0.05,
(#) - p <0.1,
(n.s.) - not significant Values represent the mean ±S.E.M. from four separate experiments. "n" is the total number of animals tested.

The microviscosity ($\bar{\eta}$) values of hippocampus and caudate from naive mice (n=20) were 5.80±0.03 and 6.10±0.05, respectively.

1. Percent of animals showing continuous and strong tremor of forelimbs (more than 70 episodes).
2. Percent of animals showing severe diarrhea with soft liquid feces.
3. Percent of animals showing more than 10 episodes.
4. Percent of animals showing more than 5 episodes.
Other symptoms such as rearing, grooming, sniffing, biting, etc. were also less prominant in the AL groups compared to saline or dipalmitoyl lecithin. In general, the AL groups were very calm most of the time and with weaker symptoms, while the diapalmitoyl lecithin groups were strange and aggressive even before the naloxone injections, and afterwards showed the most severe symptoms of all groups. Student t-test significant levels:

2. Reversal of Microviscosity of Brain Membranes of Old Animals by AL Diets

Four groups of mice were used in this experiment, in a classic T-square design. Two groups consisted of young (2-3 months) and two of old mice (24-27 months), of which group was treated with AL given in the diet (mixed with the Purina Chow) for 10-20 days. The results are shown in Table 6.

TABLE 6

Membrane lipid microvisocisty ($\bar{\eta}$) of various brain preparation from various brain regions of young (2-3 months) and old (24-28 months) Eb/Bl mice before and after treatment with AL

| Preparation | Brain Region | $\bar{\eta}$, 25° C. (poise) | | | |
|---|---|---|---|---|---|
| | | Old (AL) | Old (control) | Young (control) | Young (AL)** |
| SPM | Forebrain | 5.4 ± 0.4(20)+ | 6.4 ± 0.8(20)* | 5.0 ± 0.2(20) | 4.9 ± 0.2(6)n.s. |
| Mitochondria | " | 3.4 ± 0.3(14)+ | 4.0 ± 0.2(14)* | 3.4 ± 0.2(14) | — |
| Microsomes | " | 4.9 ± 0.3(12)n.s. | 5.1 ± 0.2(12)n.s. | 5.0 ± 0.1(12) | — |
| Crude nuclei fraction | " | 7.5 ± 0.4(12)+ | 7.9 ± 0.4(12)* | 7.5 ± 0.2(12) | — |
| Myelin | " | 9.3 ± 0.6(12)n.s. | 9.3 ± 0.4(12)n.s. | 9.1 ± 0.4(12) | — |
| Crude homogenate | " | 5.8 ± 0.1(14)+ | 6.1 ± 0.2(14)* | 5.5 ± 0.2(20) | 5.4 ± 0.2(12)n.s. |
| Dissociated Hippocrampus cells | | 6.0 ± 0.2(20)+ | 6.4 ± 0.2(20)* | 5.4 ± 0.2(24) | 5.4 ± 0.2(12)n.s. |
| Dissociated Hippocampus cells | Caudate | 6.2 ± 0.2(20)n.s. | 6.4 ± 0.2(20)* | 5.5 ± 0.2(24) | 5.5 ± 0.3(12)n.s. |

* - p <0.01 old (control as compared to young (control)
+ - p <0.01 old (AL) as compared to old (control)
n.s. - not significant
** - young (AL) compared to young (control).

The data represent the mean ±S.D. of 4-5 separate experiments, each group included 4-6 animals. Numbers in parenthesis represent the number of determinations, carried out in duplicate on samples prepared from 2 pooled animal brains.

It can be clearly seen that AL reversed the hyperviscosity of various brain preparations from old animals, especially of SPM (synaptic plasma membranes) and mitochondria, while those taken from young animals were not affected at all by AL treatment. Similar "rejuvenating" effects were found also in the binding characteristics of receptors such as serotinin receptors and in protein phosphorylation (Hershkowitz et al., Progress in Brain Research, Elsevier-North Holland, in press) in the brains of old animals, while no effects of AL treatment of young animals were observed. This fact implies that in young animals with normal membrane microviscosity, loading with lipids (e.g., AL treatment) has no effect due to efficient regulatory processes. In aged animals, however, "homeoviscous adaptation" (Sinensky, J.Cell.Biol., 85, 166 (1980)), is impaired. This implies that there is no danger of AL overdose, since excess AL is either removed or compensated for by changes in other lipids. The clinical implications of these results are obvious.

It should be mentioned that in all cases of animal treatments (by diet), no discernible toxic or side effects were observed.

Finally, it should be mentioned that protein synthesis by membrane bound ribosomes was found to be substantially decreased in the cerebellum of old animals. These changes are probably due to the changes in membrane composition and structure.

Preliminary results show that treatments of old animals with AL (in diet) caused a non-specific general increase in protein synthesis in the cerebellum of these animals.

3. The Effect of AL on the Immune Function

The main immune mechanism operating against bacterial infections, is the ingestion of bacteria by macrophages. We have followed this process after treatment with AL in vitro. The results of a representative experiment are shown in Table 7.

TABLE 7

| Number of *Staphylococcus Auereus* Colonies | | | |
|---|---|---|---|
| | 0 hour | 1 hour | 2 hour |
| Young donor #1 | 380 | 50 | 20 |
| Young donor #1 + AL | 375 | 55 | 18 |
| Young donor #2 | 385 | 62 | 17 |
| Young donor #2 + AL | 380 | 61 | 31 |
| Old donor #1 | 390 | 372 | 352 |
| Old donor #1 + AL | 375 | 150 | 92 |
| Old donor #2 | 383 | 361 | 348 |
| Old donor #2 + AL | 381 | 180 | 70 |

AL was added to whole blood (heparinized) from old or young donors to a final concentration of 400 $\mu$g/ml. The blood was then incubated at 37° C. for up to 2 hours 0.9 ml of whole blood either treated or untreated from the donors was then added to 0.1 ml of 1:1000 dilution of a 0.6 O.D. (620 nm) suspension of Staph. aureus in PBS. At indicated times 10 $\mu$l of above blood mixture was added to 5.5.3 agar maintained at 60° C. The agar-blood mixture was vortexed at high speed and poured into a petri dish and allowed to cool. The plates were incubated overnight at 35° C. and colonies counted the following morning (Kensel, et al., J.Infect.-Dis. 131, 584 (1975)).

The number of colonies indicate the number of surviving bacteria. It can be clearly seen that the number of surviving colonies was very much reduced in the cases of blood from young donors, indicating an efficient immune response. AL had no effect in these cases. In the cases of blood from old donors the number of surviving colonies only slightly decreased indicating an impaired immune response. AL had "rejuvenating" effects on the immune system which showed restoration of function. The clinical implications are obvious.

4. Effect of AL on human lymphocytes activity in vitro

Peripheral blood lymphocytes from old males (70-75 years) were mixed with irradiated lymphocytes from young (30-40 years) in a classical mixed lymphocytes assay (MLC). Sensitization of the lymphocytes was assessed by incorporation of $^3$H-thymidine. In the presence of 0.2 mg/ml AL the thymidine incorporation by the lymphocytes from old men increased by 70-300% indicating a marked increase in immunological responsiveness.

5. AL Effects on Hypertensive Rats

Spontaneously hypertensive female rats (SHR) were purchased from Charles Rivers (N.Y.) and raised locally until reaching 5 months of age. One group of 10 rats received a diet supplemented with 5% (w/w) AL for 3 weeks. The control group (9 rats) were fed in a similar manner but without AL supplementation. The mean arterial blood pressure (M.A.B.P.) was then measured. In the control group the M.A.B.P. was 125±16 (mmHg) while that of the AL treated animals was 110±12. AL significantly (p<0.05) reduced the MABP of the hypertensive rats. Concomitantly it also reduced the microvoscosity of P$_2$m membranes taken from the striatum from 6.5±0.2 poise (25° C.) to 5.5±0.2 poise. There was no significant difference between the two groups in heart rate or weight.

6. Other Effects of AL

Preliminary results indicate that the various symptoms of amphetamine-induced psychosis in rats, were eased or almost entirely eliminated by AL (done in collaboration with G. Ellison, Brain Research Ins., UCLA).

What is claimed is:

1. A composition comprising a lipid fraction derived from natural sources (AL), said lipid fraction containing 40-80 weight percent glycerides, 3-5 weight percent cholesterol, 10-30 weight percent lecithin (phosphatidyl choline), 5-15 weight percent phosphatidyl ethanolamine and 2-5 weight percent negatively charged phospholipids, wherein the ratio of unsaturated to saturated fatty acids is at least 1:1.

2. A composition according to claim 1, containing as additive an effective quantity of a physiologically acceptable antioxidant.

3. A composition comprising a lipid fraction (AL) derived from natural sources, said lipid fraction containing 60-70 weight percent glycerides, 3-5 weight percent cholesterol, 15-25 weight percent lecithin (phosphatidyl choline), 5-10 weight percent phosphatidyl ethanolamine and 2-3 weight percent negatively charged phospholipids wherein the ratio of unsaturated to saturated fatty acids is at least 1:1.

4. A composition according to claim 3 where the fatty acid composition of the lipids is the following: Palmitic acid 35-45%, oleic acid 35-45%, linoleic acid 5-10%, stearic acid 5-7%, palmitoleic acid 2-3%, arachidonic acid 0.2-1%.

5. A composition according to claim 4, wherein the ratio of unsaturated to saturated fatty acids is at least 2:1.

6. A composition according to claim 3, containing as additive an effective quantity of a physiologically acceptable antioxidant.

7. A composition according to claim 4, containing as additive an effective quantity of a physiologically acceptable antioxidant.

8. A composition according to claim 5, containing as additive an effective quantity of a physiologically acceptable antioxidant.

9. A composition according to claim 2, 6, 7 or 8 wherein said composition contains from about 0.2 to about 2 weight percent tocopherol as an antioxidant.

10. A process for the production of an active lipid fraction (AL) which comprises treating a natural lipid source with an organic liquid, in order to remove undesired lipids, collecting the precipitate and reextracting the precipitate with acetone, removing the supernatant and recovering from said supernatant the desired fraction (AL), by precipitation below 0° C.

11. A process for the production of an active lipid fraction (AL) which comprises treating a lipid source with an organic liquid, collecting the precipitate and reextracting the precipitate with acetone, removing the supernatant and recovering from the said supernatant the desired fraction (AL) by evaporation of the acetone.

12. A process according to claim 10 or 11 wherein the organic liquid is acetone.

13. A process according to claim 10 or 11 wherein the starting material is egg yolk or soybean or their crude lipid extracts.

14. A process according to claim 12, wherein the starting material is egg yolk or soybean or their crude lipid extracts.

15. A process according to claim 10 or 11 wherein the antioxidant is added to the fraction AL.

16. A process according to claim 13, wherein an antioxidant is added to the fraction AL.

17. A pharmaceutical composition for oral administration comprising as active ingredient a pharmaceutically effective amount of a composition according to claim 1, 4 or 7.

18. A pharmaceutical composition for oral administration comprising as active ingredient a pharmaceutically effective amount of a composition according to claim 9.

19. A composition according to claim 1, 3, 4 or 7, in the form of a lipid suspension in saline (10–100 mg/ml), for intravenous injections.

20. A composition according to claim 9, in the form of a lipid suspension in saline (10–100 mg/ml), for intravenous injections.

21. A composition according to claim 1, 3, 4 or 7, for oral administration wherein the lipid fraction (AL) is in a quantity of from 1 to 20 grams per unit dosage form.

22. A composition according to claim 9, for oral administration wherein the lipid fraction (AL) is in a quantity of from 1 to 20 grams per unit dosage form.

23. A composition according to any of claims 1, 4, 2 or 8, wherein the lipid fraction (AL) is in a quantity of from 0.05–2 mg/ml for in vitro treatments.

24. A method for treatment of warmblooded mammals, comprising administering a pharmaceutically effective quantity of a fraction of lipids from natural sources (AL) as recited in claims 1, 4, 2 or 8 for the treatment of the following conditions:
  a. dysfunctions of the immune system;
  b. increased vulnerability to bacterial contaminations;
  c. hypertension; and
  d. symptoms of withdrawal from morphine and alcohol.

25. A method for treatment of warmblooded mammals, comprising administering a pharmaceutically effective quantity of a fraction of lipids from natural sources (AL) as recited in claim 9 for the treatment of the following conditions:
  a. dysfunctions of the immune system;
  b. increased vulnerability to bacterial contaminations;
  c. hypertension; and
  d. symptoms of withdrawal from morphine and alcohol.

26. A method for treatment of warmblooded mammals, comprising administering a pharmaceutically effective quantity of a fraction of lipids from natural sources (AL) as recited in claim 18 for the treatment of the following conditions:
  a. dysfunctions of the immune system;
  b. increased vulnerability to bacterial contaminations;
  c. hypertension; and
  d. symptoms of withdrawal from morphine and alcohol.

27. A method for treatment of warmblooded mammals, comprising administering a pharmaceutically effective quantity of a fraction of lipids from natural sources (AL) as recited in claim 19 for the treatment of the following conditions:
  a. dysfunctions of the immune system;
  b. increased vulnerability to bacterial contaminations;
  c. hypertension; and
  d. symptoms of withdrawal from morphine and alcohol.

28. A method for treatment of warmblooded mammals, comprising administering a pharmaceutically effective quantity of a fraction of lipids from natural sources (AL) as recited in claim 20 for the treatment of the following conditions:
  a. dysfunctions of the immune system;
  b. increased vulnerability to bacterial contaminations;
  c. hypertension; and
  d. symptoms of withdrawal from morphine and other drugs.

29. A method for treatment of warmblooded mammals, comprising administering a pharmaceutically effective quantity of a fraction of lipids from natural sources (AL) as recited in claim 22 for the treatment of the following conditions:
  a. dysfunctions of the immune system;
  b. increased vulnerability to bacterial contaminations;
  c. hypertension; and
  d. symptoms of withdrawal from morphine and alcohol.

* * * * *